US008920334B2

(12) United States Patent
Stockmann et al.

(10) Patent No.: US 8,920,334 B2
(45) Date of Patent: Dec. 30, 2014

(54) METHOD OF BREATH ANALYSIS FOR DETERMINING LIVER CAPACITY OR MICROCIRCULATION USING 13C-LABELED METHACETIN SUBSTRATE

(75) Inventors: Martin Stockmann, Berlin (DE); Björn Riecke, Schwielowsee (DE)

(73) Assignees: Freie Universitaet Berlin, Berlin (DE); Charité Universitaetmedizin Berlin, Berlin (DE)

( * ) Notice: Subject to any disclaimer, the term of this patent is extended or adjusted under 35 U.S.C. 154(b) by 1405 days.

(21) Appl. No.: 11/993,817

(22) PCT Filed: Jun. 26, 2006

(86) PCT No.: PCT/DE2006/001086
§ 371 (c)(1),
(2), (4) Date: Feb. 22, 2008

(87) PCT Pub. No.: WO2007/000145
PCT Pub. Date: Jan. 4, 2007

(65) Prior Publication Data
US 2010/0143880 A1    Jun. 10, 2010

(30) Foreign Application Priority Data
Jun. 25, 2005  (DE) .......................... 10 2005 028 836

(51) Int. Cl.
| *A61B 5/087* | (2006.01) |
| *A61B 5/00* | (2006.01) |
| *A61K 49/00* | (2006.01) |
| *A61M 16/06* | (2006.01) |
| *A61B 5/097* | (2006.01) |
| *A61K 51/04* | (2006.01) |
| *G01N 33/497* | (2006.01) |
| *A61B 5/083* | (2006.01) |

(52) U.S. Cl.
CPC ............. *A61B 5/097* (2013.01); *G01N 33/497* (2013.01); *A61B 5/4244* (2013.01); *A61B 5/0836* (2013.01); *A61K 49/0004* (2013.01); *A61M 16/06* (2013.01); *A61B 5/413* (2013.01); *A61B 5/00* (2013.01); *A61K 51/04* (2013.01); *Y10S 436/90* (2013.01)
USPC ........... 600/531; 600/532; 600/133; 436/900; 436/543

(58) Field of Classification Search
CPC ... G01N 33/497; G01N 33/004; G01N 33/58; A61B 5/097; A61B 5/0836; A61B 5/0873; A61K 51/1206
USPC .......................................................... 436/900
See application file for complete search history.

(56) References Cited

U.S. PATENT DOCUMENTS

| 6,123,071 | A | 9/2000 | Berthon-Jones |
| 6,284,219 | B1 | 9/2001 | Ajami |
| 8,622,920 | B2 * | 1/2014 | Ben-Oren et al. ............ 600/532 |
| 2004/0211428 | A1 | 10/2004 | Jones et al. |
| 2005/0061321 | A1 | 3/2005 | Jones |
| 2005/0085799 | A1 | 4/2005 | Luria et al. |

FOREIGN PATENT DOCUMENTS

| DE | 225 789 | 7/1985 |
| DE | 225 789 | 8/1985 |
| EP | 0705601 A1 | 4/1996 |
| EP | 0 913 161 | 5/1999 |
| WO | 9428941 A1 | 12/1994 |
| WO | 99/30760 | 6/1999 |
| WO | 2007/054940 | 5/2007 |

OTHER PUBLICATIONS

Saadeh et al. "The utility of the 13C-galactose breath test as a measure of liver function". 2003. Aliment Pharmacol Ther. vol. 18. pp. 995-1002.*
Candelli et al. "13C-Breath Tests in the study of mitochondrial liver function". 2004. Eur Rev Med Phamacol Sci. vol. 8. pp. 23-31.*
Irving et al. "The aminopyrine breath test as a measure of liver function: a quantitative description of its metabolic basis in normal subjects". 1982. J. Lab. Clin. Med. vol. 100.*
Imamura et al. "Assessment of hepatic reserve for indication of hepatic resection: decision tree incorporating indocyanine green test". Feb. 2005. J Hepatobiliary Pancreat Surg. vol. 12. pp. 16-22.*

Becker, M. "13C breath tests for measurement of liver function". 1998. Gut. vol. 43. pp. S25-S27.*
Chlebourn and Kocha, "Isotope Selective Nondispersive Infrared Spectrometry Can Compete with Isotope Ratio Mass Spectrometry in Cumulative 13CO2 Breath Tests: Assessment of Accuracy", Klin. Biochem. Metab., 2005, v. 13, issue 34, No. 2, pp. 92-97.*
Braden et al., "13C-methacetin breath test as liver function test in patients with chronic hepatitis C virus infection", Aliment Pharmacol Ther, Jan. 2005; v. 21: pp. 179-185.*
Armuzzi, A., M. Candelli, et al. "Review article: breath testing for human liver function assessment." Aliment Pharmacol Ther (2002) 16(12): 1977-96.
Braden, B., M. Haisch, et al. "Clinically feasible stable isotope technique at a reasonable price: analysis of 13CO2/12CO2-abundance in breath samples with a new isotope selective-nondispersive infrared spectrometer." Z Gastroenterol (1994). 32(12): 675-8.
Brockmoller, J. and I. Roots "Assessment of liver metabolic function. Clinical implications." Clin Pharmacokinet (1994) 27(3): 216-48.
Candelli, M., A. Armuzzi, et al. "13C-methacetin breath test for monitoring hepatic function in cirrhotic patients before and after liver transplantation." Aliment Pharmacol Ther (2004) 19(2): 243.
Castilla-Cortazar, I., J. Prieto, et al. "Impaired intestinal sugar transport in cirrhotic rats: correction by low doses of insulin-like growth factor 1." Gastroenterology (1997) 113(4): 1180-7.
Haisch, M., P. Hering, et al. "A sensitive isotope selective nondispersive infrared spectrometer for 13CO2 concentration measurements in breath samples." Isotopes Environ Health Stud (1994) 30: 247-251.
Klatt, S., C. Taut, et al. "Evaluation of the 13C-methacetin breath test for quantitative liver function testing." Z Gastroenterol (1997) 35(8): 609-14.
Klein, P. D. "13C breath tests: visions and realities." J Nutr (2001) 131(5): 1637S-42S.
Lara Baruque, S., M. Razquin, et al. "13C-phenylalanine and 13C-methacetin breath test to evaluate functional capacity of hepatocyte in chronic liver disease." Dig Liver Dis (2001) 32(3): 226-32.
Matsumoto, K., M. Suehiro, et al. "[13C]methacetin breath test for evalucation of liver damage." Dig Dis Sci (1987) 32(4): 344-8.
Mion, F., M. Rousseau, et al. "[13C]-Galactose breath test: correlation with liver fibrosis in chronic hepatitis C." Eur J Clin Invest (1999) 29(7): 624-9.
Park, G. J., P. H. Katelaris, et al. "Valitity of the 13C-caffeine breath test as a noninvasive, quantitative test of liver function." Hepatology (2003) 38(5): 1227-36.
Schoeller, D. A., J. F. Schneider, et al. "Clinical diagnosis with the stable isotope 13C in CO2 breath tests: methodology and fundamental considerations." J Lab Clin Med (1997) 90(3): 412-21.
Zuckerman, M. J., I. S. Menzies, et al. "Assessment of intestinal permeability and absorption in cirrhotic patients with ascites using combined sugar probes." Dig Dis Sci (2004) 49(4): 621-6.
Matsumoto et al: "[13C]methacetin breath test for evaluation of liver damage" Digestive Diseases and Sciences, vol. 32, No. 4, Apr. 1987, pp. 344-348, XP002400541.
Braden B et al: "13C-methacetin breath test as liver function test in patients with chronic hepatitis C virus infection" Alimentary Pharmacology & Therapeutics, vol. 21, Jan. 2005, pp. 179-185, XP002400542.
Schneider J F et al: "Validation of 13C02 breath analysis as a measurement of demethylation of stable isotope labeled aminopyrine in man" Clinica Chimica Acta, vol. 84, Jan. 1978, pp. 153-162, XP002400543.
Pauwels S et al: "Breath 14C02 after intravenous administration of [14C]aminopyrine in liver diseases" Digestive Diseases and Science, vol. 27, No. 1, Jan. 1982, pp. 49-56, XP002400544.
Lingenfelser, T, et al."Evaluation of microsomal liver function . . . " (1999) 29 Suppl. 1 Abstract 60, European Society for Clinical Investigation, Abstracts and index of the 33rd ESCI meeting, Apr. 8-10, 1999, Milan Italy.
Lingenfelser et al. "Intravenous (13C)-methacetin breath test for evaluation of liver function in cirrhotic patients and healthy controls", Gastroenterology, 1998, Elsevier, Philadelphia.
Watkins et al. "Diagnosis and differentiation of Fat Malabsorption in Children Using 13C-Labeled Lipids: Trioctanoin, Triolein, and Palmitic Acid Breath Tests", Gastroenterology, 1982, vol. 82, No. 5, p. 911-917.
"The Merck Index", An Encyclopedia of Chemicals, Drugs and Biologicals, Eleventh Edition, 1989, p. 39, Merck & Co., Inc., Rahway, New Jersey.
Caspary et al. "Klinische Bedeutung des I4C-Glykocholat-Atemtests in der gastroenterologischen Diagnostik bei Erkrankungen mit gesteigerter Dekonjugation von Gallensauren", DMW, 1976, pp. 353-360.
European Examination Report dated Jul. 28, 2010, as issued in connection with corresponding European Patent Application No. 06761702.7.
AU Office Action dated Mar. 28, 2012 as received in application No. 2006264108.
European Examination Report dated Jul. 6, 2011 as received in related application No. 06 761 702.7.
Stockmann, Martin: "Habilitation treatise: Quality rating of a newly developed method for determining the liver function within liver surgery (LiMAx Test)", 2009, pp. III, IV, 7 to 12 and 32 to 36.
Indian Office Action for Indian Application No. 321/KOLNP/2008, mailed Apr. 30, 2014.

* cited by examiner

*Primary Examiner* — Yelena G Gakh
(74) *Attorney, Agent, or Firm* — Maschoff Brennan (57) ABSTRACT

The invention relates to an analysis method for determining a functional parameter of an organ of a human or animal individual by measuring the $^{13}CO_2$ content in the air exhaled by the individual to which a substrate has been administered the reaction of which in the body of the individual enriches the air exhaled by the individual with $^{13}CO_2$. The method is characterized by using a measuring device, the maximum reaction rate of the substrate in the body of the individual being determined via a change of the measured $^{13}CO_2$ content in the air exhaled by the individual using zero-order enzyme kinetics. The invention also relates to an aqueous methacetin solution for use in said analysis method, the pH of the solution being greater 7.0. The invention also relates to a face mask (1) for use in the inventive method for separating the exhaled air from the air inhaled by an individual. Said face mask comprises a face mask body (2) and an air cushion (3) encircling the face mask body. Said air cushion is filled with a gas and establishes a substantially gas-tight contact between the face of the individual and the face mask (1) placed on the face of the individual so that the air required by the individual for breathing and the air exhaled by the individual has to flow essentially completely through the face mask (1). At least one exhalation valve (5) and at least one inhalation valve (4) are integrated into the face mask and allow a flow of inhaled and exhaled air through the face mask. The invention finally relates to a diagnostic method for determining the functional parameters of an organ of a human or animal individual.

12 Claims, 5 Drawing Sheets

METHOD OF BREATH ANALYSIS FOR DETERMINING LIVER CAPACITY OR MICROCIRCULATION USING 13C-LABELED METHACETIN SUBSTRATE

FIELD

The invention relates to an analysis method for determining a functional parameter of an organ, to an aqueous methacetin solution, suitable for this analysis method, to the use of this methacetin solution, to a respiratory mask, for use in an analysis method according to the invention, and to a diagnostic method, for determining a functional parameter of an organ.

BACKGROUND

The determination of a functional parameter of an organ, in particular the quantitative determination of liver function, is of great importance in many areas of medicine. Chronic liver diseases are widespread in Europe, with 8.9 million people affected by hepatitis C. As their disease progresses, these individuals or patients find themselves in most cases under permanent medical care. In the therapy and management of patients with chronic liver diseases, quantifying the liver function can greatly improve the therapy control, and assessment of liver function is crucial in ensuring that the correct therapeutic decisions are made.

Partial liver resection is a common method used in surgery today. It is performed as a segmental resection or hemihepatectomy along the anatomical margins. Extensive interventions in the parenchymatous organ were made possible by the development of a wide variety of operating techniques. The post-operative morbidity and mortality after liver failure, however, is still a considerable problem, due to inadequate liver function capacity resulting from previously damaged liver tissue or from there being too little liver tissue remaining. Many of the surgical procedures, however, have to be performed in previously damaged liver tissue, in most cases where the liver has been transformed by cirrhosis. It is therefore necessary to be able to determine the functional liver capacity of a patient before the partial liver resection, so as to ensure that patients who no longer have sufficient functional reserves of liver tissue are not subjected to what is for them a high-risk operation or are not assigned to other treatment methods.

Assessment of liver function is of particular importance in liver transplantation, since here the organ function has to be assessed without delay and a treatment decision has to be made quickly. In many clinical situations, it is also difficult to assess whether there is a parenchymatous disturbance or whether other causes are responsible for the clinical symptoms presented by the patients. In summary, therefore, there is a great need for a genuinely quantitative liver function test for broad application in medicine.

Efforts are therefore being made across the world to develop simple tests that allow prognostic statements to be made concerning the functional reserves of liver cell tissue. Conventional laboratory parameters are very unreliable and therefore unsuitable for this purpose. They are not sufficiently sensitive to permit reliable evaluation of the complex biological processes in the hepatocyte (biosynthesis, biotransformation, catabolism of xenobiotics, etc.) and of the changes in these processes in the presence of disease.

In addition, they are subject to a large number of external influences and are distorted by these. For example, they are to some extent distorted by the required therapeutic intervention, by replacement of human plasma, clotting factors or albumin, and can thus not be used as liver function parameters. Many different liver function tests have been described in the literature (Matsumoto, K., M. Suehiro, et al. (1987): "[$^{13}$C]methacetin breath test for evaluation of liver damage." Dig Dis Sci 32 (4): 344-8, 1987; Brockmoller, J. and I. Roots (1994): "Assessment of liver metabolic function. Clinical implications." Clin Pharmacokinet 27 (3): 216-48).

However, it has not hitherto been possible, with any test method, to make valid and genuinely quantitative statements on liver function. In all methods to date, it was possible only to make a significant differentiation between different disease groups with already clinically detectable signs. Consequently, in clinical practice, no liver function test is employed in routine diagnostics, since these tests do not afford any additional clinical benefit based on their present accuracy.

The $^{13}$C-methacetin breath test used hitherto, with an exclusively oral administration of the substance, is a method which can distinguish between the liver function capacity of healthy subjects and that of patients with chronic hepatitis without cirrhosis and with cirrhosis in the different Child-Pugh stages (Matsumoto, K., M. Suehiro, et al. (1987): "[$^{13}$C]methacetin breath test for evaluation of liver damage." Dig Dis Sci 32 (4): 344-8, 1987), but does not permit a genuine quantification.

The substance methacetin is demethylated to paracetamol in a rapid one-step reaction by the enzyme CYP1A2 in the liver, with $CO_2$ subsequently being produced. By $^{13}$C-labeling of the methyl group bonded via the ether bridge, $^{13}CO_2$ can then be measured in the exhaled air. The following formula (I) represents the structural formula of methacetin:

The aim of genuine quantification with an individual measurement result cannot be achieved using the previous methods. There are two reasons for this:

1. The basis for statements derived from a breath test is that the step to be evaluated in the cascade of processes of absorption and metabolism has to be the step that determines the reaction rate. In the previous methods for evaluating the liver function (oral administration of the test substance), however, the rate-determining step is in most cases the absorption, not the conversion of the substrate in the liver.
2. To be able to make quantitative statements on the basis of an enzyme system (in the present case: to be able to determine the maximum liver function capacity, that is to say the functional liver capacity), the enzyme system to be tested has to be fully utilized at least in the short term. Only in this case does the reaction proceed independently of the substrate concentration.

For a genuine quantification, therefore, it is imperative to reach substrate surplus. If this is not achieved, the reaction rate is directly proportional to and therefore dependent on the substrate concentration, which for its parts drops non-linearly. A quantitative statement on functional capacity is impossible. In all studies using oral test substances, no genuine quantification could therefore take place, because full enzyme utilization is not achieved with the previous methods. This has the following causes:

1. When used orally, methacetin must first pass through the stomach and be transported as far as the duodenum and the proximal jejunum in order to be absorbed. Only then can the substance reach the liver by way of the portal vein. In principle, this process costs time and results in delayed and incomplete inundation in the liver. This is extremely variable and is influenced by numerous physiological and pathological conditions. For example, in cirrhosis of the liver, in which liver function tests could be used for staging and for therapy management, the intestinal transit and absorption is greatly changed (Castilla-Cortazar, I., J. Prieto, et al. (1997): "Impaired intestinal sugar transport in cirrhotic rats: correction by low doses of insulin-like growth factor I". *Gastroenterology* 113 (4): 1180-7). In the period following abdominal operations too (e.g. liver resections or liver transplants), intestinal atony (paralytic ileus) means that no reliable statement can be made at all.
2. A sufficient dose of the test substance is necessary. With too low a dose, as in most methods for carrying out the oral methacetin breath test, full utilization of the enzyme system per se is not achieved.

It should also be noted that methacetin is extremely sparingly soluble in water or in an aqueous buffer. It crystallizes out of a usually aqueous solution within a period of hours to days. Such a solution can be used only, if indeed at all, for oral administrations of methacetin. Other administration forms are not possible.

Moreover, in the previous methods, the percentage recovery rate of the applied dose (dose %/h) and the cumulative dose are analyzed at specific times or time intervals in order to determine the liver function. The calculation of the dose %/h does not absolutely define the reacted substrate quantities and also does not take account of the individual bodyweight of the patient. It is not possible in this way to individualize and thus standardize the results in order to class the maximum functional liver capacity into a standard population.

The previous determination of the metabolized cumulative dose $D_{kum}$ over a defined period of time is equally inexpressive in respect of functional liver capacity. For a reliable statement concerning the maximum conversion of the enzyme system over time, said system would have to be fully utilized over the entire period. For the reasons mentioned above, this is not the case. Consequently, the presently used calculation of the cumulative dose cannot be used for quantifying the functional liver capacity.

To transfer the air exhaled by an individual into a measurement device, it is recommended to use a respiratory mask which is placed onto the face of the individual. For the subsequent reliable conduct of an analysis method, it is critically important that the exhaled air is safely separated from the inhaled air and, in addition, that unforced breathing by the individual is permitted by a low airway resistance of the respiratory mask.

Various types of respiratory masks are in common use in medicine, in occupational safety and also in diving. In medicine, this is the case in the induction and performance of anesthesia or also for respiratory therapy and noninvasive ventilation. Masks with a good matching shape and a tight fit are preferred, and the required valves are fitted outside the masks, in the tube systems or in the other connected appliances.

Valves are installed in some masks used in occupational safety and also in masks used in diving, but the focus here lies in the delivery of respiratory gas and in the secure sealing of the system. High airway resistance generally arises in these cases, with the result that, for example, a medical test is needed to ensure suitability before occupational use of such a system.

To analyze certain constituents in the exhaled air, it is necessary to separate the respiratory gas path as close as possible to the site of origin of the exhaled substances, i.e. as close as possible to the pulmonary alveoli. Otherwise, the inhaled air and the exhaled air mix together. Moreover, the separation must not cause any substantial increase in airway resistance, especially not in the case of patients whose pulmonary function is compromised for whatever reason. The inhalation resistance specifically should not substantially increase, since the respiratory work or the supply of gas cannot be mechanically assisted as it is, for example, in anesthesia, ventilation, or in diving equipment or occupational safety equipment. Moreover, it is of great importance to establish, during the analysis, whether the respiratory mask is sitting tightly on the face or has possibly just been taken off.

SUMMARY

The object of the invention is to make available a reliable analysis method for determining a functional parameter of an organ of an individual and also a corresponding diagnostic method, and to make available a methacetin solution in which dissolved methacetin remains stably dissolved over a period of weeks or months and can thus be used as a substrate in the methods according to the invention.

This object is achieved by an analysis method, for determining a functional parameter of an organ of a human or animal individual. According to this analysis method, the $^{13}CO_2$ content in the air exhaled by the individual is measured, the $^{13}CO_2$ in the body of the individual being formed enzymatically from a substrate that has been administered beforehand to the individual, and then being exhaled by the individual. The measurement of the $^{13}CO_2$ content in the air exhaled by the individual is carried out using a suitable measurement device. The maximum reaction rate of the substrate in the body of the individual is determined via a change of the measured $^{13}CO_2$ content in the air exhaled by the individual using zero-order enzyme kinetics. The analysis method according to the invention therefore proceeds from a consideration of enzyme kinetics.

The functional parameter of an organ that is to be determined is preferably the liver function capacity and/or the microcirculation in the liver. Thus, the analysis method is suitable in particular for quantifying the functional liver capacity of the individual. The function of the liver, as the central organ of metabolism, is extremely complex. Many biochemical synthesis and degradation processes take place in the liver. A common feature, however, is that almost all of them function on the basis of an enzymatic metabolism.

The $^{13}CO_2/^{12}CO_2$ ratio in the air exhaled by the individual is preferably determined. This value can be used as the $^{13}CO_2/^{12}CO_2$ ratio in the formula (1) below.

In a particularly preferred embodiment of the invention, the maximum reaction rate (LiMAx) is calculated through the converted quantity of substrate per unit of time in µg/h/kg bodyweight at variable times at which the maximum value is reached, such that genuine quantification of the maximum functional liver capacity can be made. The calculation is carried out according to the following formula (1), which describes zero-order enzyme kinetics:

$$LiMAx = \frac{(\delta^{13}C_{tmax} - \delta^{13}C_{10}) \cdot R_{PDB} \cdot P \cdot M}{KG} \quad [\mu g/h/kg] \qquad (1)$$

Here, $\delta^{13}C$ is the difference between the $^{13}CO_2/^{12}CO_2$ ratio of the sample and the Pee Dee Belmite (PDB) standard in delta per mil, $R_{PDB}$ is the $^{13}CO_2/^{12}CO_2$ ratio of the PDB standard (0.0112375), P is the $CO_2$ production rate (300 mmol/h×surface area of body in $m^2$), M is the molecular weight of the substrate, and KG is the actual bodyweight of the individual in kg.

In another preferred embodiment of the invention, it is not the $^{13}CO_2/^{12}CO_2$ ratio, but the absolute $^{13}CO_2$ content that is determined in the air exhaled by the individual. This is possible, for example, by means of isotope-selective infrared spectroscopy. In the formula (1), the absolute $^{13}CO_2$ volume concentrations integrated over time are then used directly instead of the $^{13}CO_2/^{12}CO_2$ ratios, and it is therefore also possible to omit the factors $R_{PDB}$ and P and, consequently, the dependence of the merely generally estimated $CO_2$ production rate. The $^{13}CO_2$ volume concentration represents the concentration of the $^{13}CO_2$ in the whole of the exhaled air, that is to say that, in the preferred use of the $^{13}CO_2$ content in the air exhaled by the individual, the volume of the entire respiratory gas stream is determined in addition to the $^{13}CO_2$ concentration. This also yields the rate of metabolism (μg/h/kg), that is to say the converted quantity of substrate per unit of time, standardized to the bodyweight of the individual.

The formula (1) is simplfied to the formula (2) when determining the absolute $^{13}CO_2$ concentration:

$$LiMAx = \frac{\int_{t=tmax}^{t=tmax+i} [^{13}CO_2] dt \cdot \int_{t=tmax}^{t=tmax+i} \dot{V} dt \cdot M}{KG} \quad [\mu g/h/kg] \qquad (2)$$

Here, $[^{13}CO_2]$ is the absolute concentration of the $^{13}CO_2$ per unit of volume in the air exhaled by the individual, $\dot{V}$ is the volume per unit of time, t is the time, $t_{max}$ is the time of maximum metabolism, i is the smallest possible time resolution according to the measurement method, M is the molecular weight of the substrate, and KG is the current bodyweight of the individual in kg.

An infrared spectrometer is preferably used to determine the $^{13}CO_2$ content in the exhaled air, since $^{13}CO_2$ has an absorption band easily separated in the infrared range.

In NDIRS measurement devices (NDIRS=nondispersive infrared spectroscopy), the water vapor contained in the exhaled air is removed before the measurement, advantageously by a humidity exchanger connected upstream of the measurement device, in order to avoid undesired absorption of the water vapor in the infrared range. A particularly suitable humidity exchanger is, for example, a Nafion humidity exchanger. However, other humidity exchangers that are able to effectively dry the air exhaled by the individual are also similarly suitable.

In isotope-selective determination of the absolute $^{13}CO_2$ content in the air exhaled by an individual, this drying of the exhaled air to be analyzed is preferably omitted, since the bands of the water vapor are not superposed with the $^{13}CO_2$ band or bands to be observed.

In a preferred embodiment of the invention, not only is the maximum reaction rate of the substrate in the body of the individual determined, but also the inundation time, that is to say the time necessary to reach the maximum reaction rate.

The inundation time is preferably used to assess the microcirculation in the liver, so as to be able to detect microcirculation disturbances. Assuming the quickest possible inundation time by in particular intravenous bolus injection and substrate excess and the high first-pass effect of methacetin or another substrate, the hepatic microcirculation can be assessed particularly advantageously. The inundation time needed to reach the maximum reaction rate $t_{vmax}$ is determined, said inundation time lengthening in the presence of microcirculation disturbances, since in this case the substrate inundation is not uniformly or completely delayed in all areas of the liver. Liver perfusion can thus be assessed.

The microcirculation and the liver perfusion are preferably not just assessed in isolation, but also assigned to a standard population. To do so, the inundation time is standardized to a normal population taking into account the bodyweight of the individual. The same applies also to the maximum reaction rate. By the reference to the individual bodyweight, it is possible to eliminate an interindividual variability and thus achieve a standardization. Only in this way is it possible to class the individual functional liver capacity into a comparison population. With the method according to the invention, it is not only possible to differentiate between limited liver function (e.g. in manifest cirrhosis of the liver) and healthy liver performance; instead, as a result of the rapid and complete utilization of the enzyme system, very slight differences in the maximum reaction rate (functional liver capacity) can now be determined over a wide measurement range.

To be able to detect the time of the maximum reaction rate, it is necessary to analyze the $^{13}CO_2/^{12}CO_2$ ratio and the relative or absolute $^{13}CO_2$ content in the exhaled air over time.

Therefore, samples of respiratory gas are preferably collected discontinuously at defined times and are analyzed with a respiratory gas analyzer (measurement device) according to one of the techniques described above. For example, the respiratory gas samples can be collected at the times 0 min and 2½, 5, 10, 15, 20, 30, 40, 50 and 60 min after the application of the test substance (substrate). This measurement method is also referred to as discontinuous offline measurement. The measurement of the respiratory gas samples, that is to say of the exhaled air to be analyzed, can be carried out directly when the samples are collected or after a delay time. In other words, the collected samples of respiratory gas can be temporarily stored prior to a measurement, for example if no measurement device is immediately available for use.

It is ideal, and preferable, to perform a continuous analysis of the exhaled air using a respiratory gas analyzer as measurement device (online measurement).

The measurement preferably extends over a time interval in which the enzyme kinetics proceed or the shortest time interval within which a reliable determination of the enzyme kinetics takes place. In diseased individuals, an analysis for a time interval of about 60 minutes is necessary. In healthy individuals, in whom the maximum reaction rate of the substrate in the liver is reached after just a few minutes, the analysis method can be terminated once the maximum reaction rate has been reached, that is to say after a few minutes (for example 5 minutes).

The continuous online measurement of the $^{13}CO_2$ content in the air exhaled by the individual results in particular in a considerable saving in time in the examination of healthy individuals since, in the offline measurement, the respiratory samples are first of all collected and thereafter analyzed, such that early termination of the analysis method is not really possible. In diseased individuals too, however, there is still a distinct saving in time, since the result of the measurement is available immediately upon conclusion of the measurement, and forwarding to a laboratory, or a renewed intervention by the operator, is not needed.

As a result of an increased time resolution in continuous online measurement compared to the discontinuous offline measurement, more data points are obtained, which results in greater precision of the analysis of the curves.

Since, in continuous online measurement, no respiratory gas bag has to be inflated at set times, there is no dependency on the operator in respect of said times; the data points can thus be assigned, with a significantly reduced error, to a point in time within the proceeding enzyme kinetics.

The continuous online measurement is also preferred for the reason that it permits fully automatic measurement, especially if, by suitable measures, the gas delivery (i.e. the correct fit of a respiratory mask on the face of the individual) is guaranteed.

The air exhaled by the individual is preferably collected at the individual's face by means of a respiratory mask, in particular a respiratory mask having the features explained further below in the description, and is transferred from here through a tube or other connecting line into the measurement device, in order to then perform the analysis method.

In a particularly preferred embodiment of the invention, the substrate used is $^{13}C$-labeled methacetin. This $^{13}C$-methacetin has a molecular weight of 166.19 g/mol.

In the reaction of $^{13}C$-methacetin in the body of the individual, a liver-specific enzyme system is tested which, however, does not occur in such great ratio that complete utilization of the enzyme could be achieved at any time. The cytochrome p-450 isoenzyme CYP1A2 is therefore suitable. Only relatively few substances are metabolized by CYP1A2, such that the factors influencing and disturbing it are small. Nevertheless, it is to be regarded as representative of the liver function.

The substance methacetin is demethylated to paracetamol by CYP1A2 in a rapid one-step reaction, with $CO_2$ then resulting. A rapid and complete reaction is ensured by the high first-pass effect. $^{13}C$-methacetin is thus eminently suitable. By $^{13}C$-labeling of the methyl group bonded via the ether bridge, $^{13}CO_2$ can then be measured in the exhaled air. This can be done by analyzing the exhaled air using a suitable respiratory gas analyzer. Suitable methods for this purpose are, for example, isotope-selective nondispersive infrared spectroscopy or isotope-selective mass spectroscopy. With both methods, the measured value provided is the difference of the $^{13}CO_2/^{12}CO_2$ ratio of the sample and the Pee Dee Belmite (PDB) standard in delta per mil ($\delta^{13}C$).

The object of the invention is also achieved with an aqueous methacetin solution. Accordingly, the pH value of the solution is set such that the solution is basic, with a pH value of 7.5 to 9.5 and in particular of 8.0 to 8.5 being particularly preferred. Thus, for example, a pH value of 8.2 has proven particularly advantageous.

To better dissolve the methacetin, the methacetin solution preferably contains a solubilizer.

Propylene glycol has particularly advantageous solubilizing properties, and it is at a concentration of preferably 10 to 100 mg/ml, more preferably of 20 to 50 mg/ml, particularly preferably of 25 to 35 mg/ml, and very particularly preferably of 30 mg/ml, that said advantageous solubilizing properties of the propylene glycol come to the fore.

In a preferred variant of the invention, the methacetin solution is sterile and/or pyrogen-free, such that the methacetin solution can be administered to a human or animal individual or patient without fear of health-related complications.

The methacetin in the methacetin solution preferably has a concentration of 0.2 to 0.6% (w/v), particularly preferably of 0.3 to 0.5%, and very particularly preferably of 0.4%. At this concentration, the methacetin in the methacetin solution according to the invention is readily soluble. At lower concentrations, preferred in respect of solubility, the volume of the methacetin solution that has to be administered to a test individual increases significantly, which is undesirable. At a higher methacetin concentration, by contrast, there is a danger of the methacetin precipitating or crystallizing out of the solution.

In order to advantageously use the methacetin solution for performing a breath test for determining functional parameters of an organ, the dissolved methacetin is preferably labeled with the carbon isotope $^{13}C$. This labeling is preferably restricted only to those areas of the molecule which are released as $CO_2$ upon reaction in the body of an individual. This is the methyl group shown at the left margin in formula (I). By limiting the $^{13}C$ labeling to this methyl group, products of the breakdown of methacetin other than $CO_2$ have no labeling, such that these breakdown products do not interfere with measurements that are based on the determination of the content of $^{13}CO_2$.

The invention also relates to the use of a methacetin solution according to the invention in an analysis method for determining the functional parameter of an organ of a human or animal individual.

A further aspect of the invention is the use of a methacetin solution according to the invention in an analytical or diagnostic method for determining the dynamic distribution of methacetin in an organ of an individual by means of nuclear magnetic resonance spectroscopy (NMR) or magnetic resonance therapy (MRT). Since $^{13}C$ is NMR-active, it is recommended to investigate the dynamic distribution of methacetin in the liver, for example, in order to be able to draw conclusions regarding liver damage. In such a method, dynamic processes in the liver can be investigated with relatively high time resolution (in the minute range). Liver areas not accessible to a through-flow of methacetin are only inadequately supplied, if at all, with other substances too, such that a correlation to (partial) liver damage can be drawn in this way.

The object is also achieved by a respiratory mask, for separating the exhaled air from the inhaled air of an individual, since such a respiratory mask is particularly suitable for conveying the air exhaled by an individual into a measurement device, which air is analyzedf in the latter in an analysis method according to the invention. Such a respiratory mask has a respiratory mask body and a gas cushion, which extends around the respiratory mask body and is arranged between the face of the individual and the respiratory mask body during operation.

The gas cushion is filled with gas and permits a substantially gas-tight contact between the face of the individual and the respiratory mask, which is arranged on the face of the individual. This gas-tight contact ensures that inhaled air required by the individual and exhaled air exhaled by the individual is guided substantially completely through the respiratory mask. Inhaled air or exhaled air does not in practice flow under the gas cushion into the area surrounded by the respiratory mask, but only through inhalation and exhalation valves, specifically at least one exhalation valve and at least one inhalation valve that are integrated directly into the respiratory mask.

The basic shape of the respiratory mask body is preferably produced in different sizes to match the size of face of the individual who is to wear the mask (e.g. for children, small adults, medium-sized adults, large adults, very large adults, etc.), so as to permit a secure fit of the respiratory mask on a large number of face shapes.

The gas cushion preferably has a valve, which can have a Luer connector for example, or a similar closure piece. By means of this valve or closure piece, the degree of filling of the gas cushion can be adjusted in order to further optimize the secure fit of the respiratory mask on the face of the individual.

Air in particular is recommended as the gas with which the gas cushion is filled. However, other gases can equally be used as the gas for filling the gas cushion, but these gases should be noncombustible and nontoxic, so as to minimize the risk of injury to the individual wearing the mask.

The solid plastic housing of the respiratory mask body additionally comprises a solid, conical attachment for an oxygen tube, so as to be able, when necessary, to supply the individual wearing the mask additionally with oxygen or other added gas mixtures.

In a preferred embodiment of the invention, the inhalation valve and exhalation valve are installed fixedly in the respiratory mask body.

In an alternative embodiment of the invention, the valves can be separately removed from the respiratory mask body and are clipped into a matching conical fixture in the respiratory mask body, as a result of which a gas-tight connection is established between the inhalation/exhalation valve and the respiratory mask body.

The inhalation and exhalation valves are preferably composed of a thin and flexible, but sufficiently stiff membrane that covers through-openings formed in the valve for the through-flow of gas or air. The membrane can preferably be made of silicone, but can also be made of other materials that satisfy said criteria.

For conveying the separated exhaled air to an analysis or measurement device, for example via a special tube, the exhalation valve preferably has an attachment for carrying off the separated exhaled air.

To ensure that the separated exhaled air is carried off from the exhalation valve in a uniform manner, the attachment for carrying off the exhaled air is particularly preferably arranged centrally on the exhalation valve.

The attachment is preferably a conical attachment with an internal diameter of 20 to 30 mm at its narrower opening, an internal diameter of 22 mm being particularly preferred. Such a (standardized) attachment permits uncomplicated connection of a tube or other withdrawal device to the attachment of the exhalation valve.

The main body of the respiratory mask preferably has a securing device for securing at least one holding element, by means of which the respiratory mask can be securely held on the face of the individual. The securing device can, for example, be a hole that is suitably sealed off to ensure that no air passes through the hole into the area surrounded by the respiratory mask. The securing device is advantageously connected only to the outside wall of the respiratory mask body and has the shape of a ring, a nipple or an eyelet. The securing device can, for example, be injection molded onto the respiratory mask body.

The holding element is preferably a rubber band, the length of which can be varied if appropriate in order to ensure a secure fit of the respiratory mask on the face of the individual. A rubber band for holding the respiratory mask is fitted particularly preferably in each case in the mouth area and nose area.

A respiratory mask with the features discussed above is particularly suitable for use in an analysis method or in a method for determining the functional parameter of an organ of a human or animal individual.

A pressure sensor is preferably integrated into the gas cushion and is connected via a cable to a plug connection in the area of the attachment on the exhalation valve. By means of this pressure sensor, it is possible to reliably detect whether the respiratory mask is fitted in place or not. The contact pressure provided by the rubber bands leads to an increase in pressure in the air cushion. By means of this change in pressure, and the time profile, it is possible to determine the times at which the respiratory mask is fitted tightly in place. Similarly, removal of the respiratory mask, for example by the individual, can be automatically registered. This control possibility afforded by the integrated pressure sensor is also conceivable in many situations and in other respiratory masks with air cushions (e.g. in intensive care medicine).

The data measured by the pressure sensor integrated in the respiratory mask can be evaluated by an interconnected online measurement device, that is to say a measurement device suitable for a continuous online measurement.

The object of the invention is also achieved by use of the respiratory mask according to the invention in an analysis method according to the invention, since the respiratory mask ensures a safe and reliable provision of the exhaled air that is to be analyzed at the measurement device, such that the analysis method can be reliably performed.

The object of the invention is also achieved by a diagnostic method, for determining the functional parameter of an organ of a human or animal individual or patient. This method involves an intravenous injection of a $^{13}$C-labeled methacetin solution according to the invention into the body of the individual, and thereafter an analysis of the relative and/or absolute $^{13}CO_2$ content in the air exhaled by the patient, using an analysis method according to the invention that has already been explained above.

The functional parameter of an organ to be determined is preferably the liver function capacity and/or the microcirculation in the liver.

The rapid substrate inundation required for the enzyme-kinetic evaluation is ensured by the fact that $^{13}$C methacetin is administered intravenously in a bolus. The intravenous bolus injection ensures an immediate and complete substrate inundation in the liver. The absorption of the test substance $^{13}$C-methacetin is no longer the step that determines the reaction rate. With the preferred dose of 2 mg methacetin per kg bodyweight, a temporary enzyme utilization is also permitted in patients with a healthy liver by a short-term substrate excess. This permits the actual quantitative expressiveness, since zero-order enzyme kinetics are achieved, and only this permits a statement concerning the maximum functional capacity of an enzyme system.

The stable intravenous administration of the sparingly water-soluble $^{13}$C-methacetin in a concentration sufficient for bolus injection is preferably achieved by the $^{13}$C-methacetin being dissolved in a concentration of 4 mg/ml in water for injection and the addition of 30 mg propylene glycol per ml and the setting of a basic pH value of 8.5. The solution is prepared sterile and pyrogen-free, and its osmolarity is set such that its administration to the individual to be tested can be performed without difficulty through a peripheral vein.

BRIEF DESCRIPTION OF THE DRAWINGS

The invention will be explained in more detail on the basis of the following figures and of an illustrative embodiment, without these explanations limiting the scope of protection of the invention.

DETAILED DESCRIPTION

Figure 1:
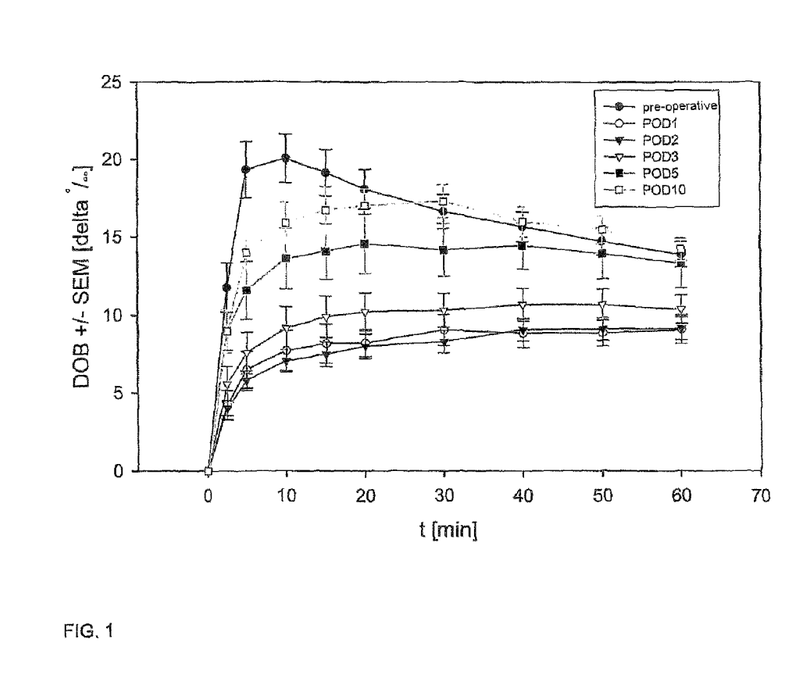
FIG. 1 is a graph showing the mean delta-over-baseline values over time in a liver function study on patients who had undergone a partial liver resection.
Figure 2:
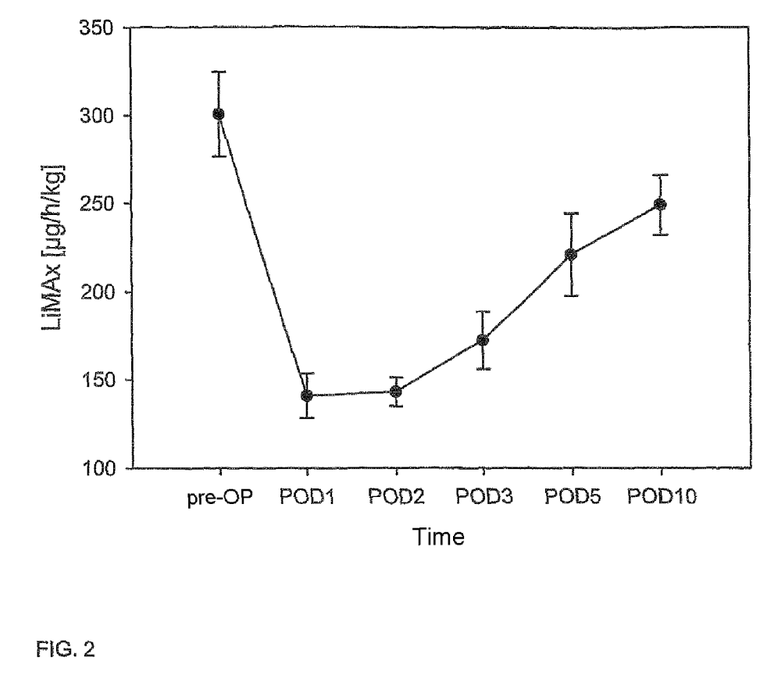
FIG. 2 is a graph showing the actual functional mean liver capacities (LiMAx), calculated from the data in FIG. 1, as a function of time.
Figure 3:
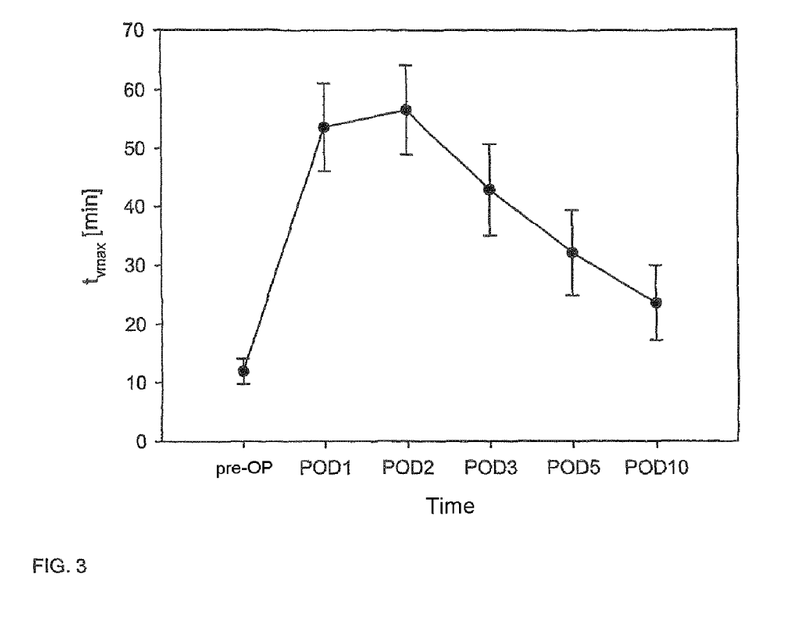
FIG. 3 is a graph showing the mean inundation time of the substrate $^{13}C$-methacetin in the liver as a function of time, for determining the micro-circulation in the liver.

FIGS. 1 to 3 will be explained in more detail on the basis of the following illustrative embodiment.

EXAMPLE 1

In the context of a prospective study, a method, which is discussed in more detail below, was used to evaluate liver function before and after partial liver resection in a number of patients:
1. Method and means for enzyme-kinetic quantification of liver function capacity and for assessment of microcirculation disturbances of the liver, characterized in that
   a) A special intravenous ready-to-use solution of $^{13}C$-labeled methacetin is injected intravenously in a sufficient dose to ensure rapid inundation of the substance in the liver, with substrate surplus on the metabolizing enzyme system.
   b) By analyzing the $^{13}CO_2/^{12}CO_2$ ratio in the exhaled air over a period of time of one hour following injection, the maximum reaction rate of the $^{13}C$-labeled methacetin is determined using zero-order enzyme kinetics.
   c) By standardizing to the individual bodyweight, comparability with a normal population is provided.
   d) Microcirculation disturbances in the liver can be assessed by determining the inundation time until the maximum reaction rate is reached.
2. Method according to point 1, characterized in that a $^{13}C$-labeled methacetin solution is used in a concentration of 0.4%.
3. Method according to points 1 and 2, characterized in that the $^{13}C$-labeled methacetin solution contains 30 mg/ml of propylene glycol for stabilization, and the pH value is basic.
4. Method according to points 1 to 3, characterized in that the $^{13}C$-labeled methacetin solution is sterile and pyrogen-free.
5. Method according to points 1 to 4, characterized in that the $^{13}CO_2/^{12}CO_2$ ratio is ideally determined continuously, or otherwise at the defined times of 0 min and 2½, 5, 10, 15, 20, 30, 40, 50 and 60 min after injection of the $^{13}C$-labeled methacetin.

From the prospective study, FIG. 1 shows the curves of the mean delta-over-baseline (DOB) values of the $^{13}CO_2/^{12}CO_2$ ratio in the air exhaled by the patients at the individual measurement times, plotted over time.

In the pre-operative stage, where there is a normal and maximum functional liver capacity, the curve rises steeply, then falls again after the maximum value is reached. After partial liver resection, the curve changes drastically on post-operative day 1 (POD1) to saturation kinetics with markedly reduced maximum function. As liver regeneration increases after the partial liver resection, the curve changes back again toward the pre-operative curve (POD3-10).

The actual functional liver capacity calculated from this in µg/h/kg is shown in FIG. 2. On POD1, the maximum functional liver capacity (LiMAx) falls from 301±24 µg/h/kg to 141±13 µg/h/kg, thereafter slowly regenerating back to a value of 249±17 µg/h/kg on post-operative day 10 (POD10).

The analysis of the microcirculation, represented in FIG. 3, shows a marked disturbance after the partial liver resection, in parallel with a prolongation of the inundation time ($t_{vmax}$) from 11.9±2.17 min to 53.5±7.51 min, which subsequently recovers again.

Figure 4:
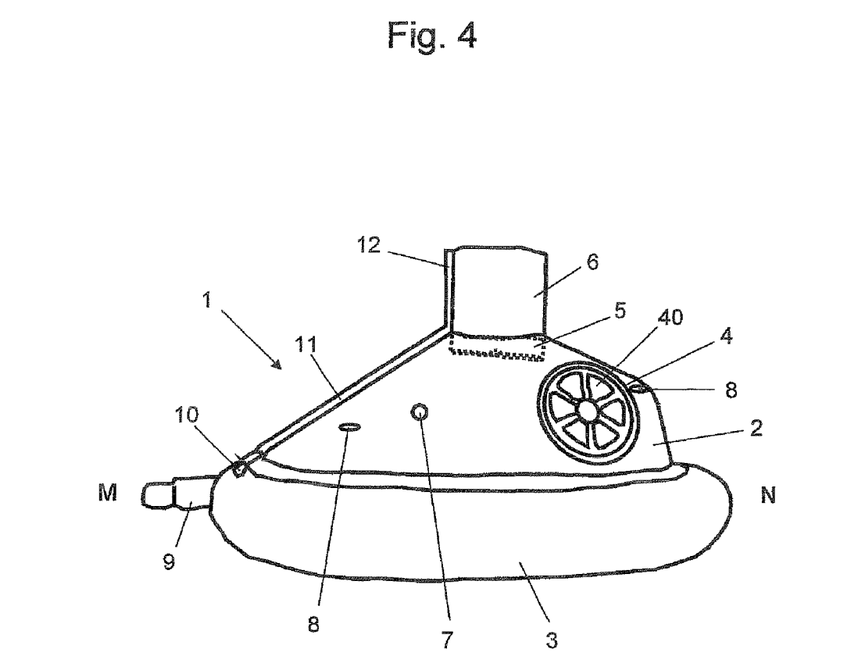
FIG. 4 is a side view of an illustrative embodiment of a respiratory mask according to the invention.

FIG. 4 shows an illustrative embodiment of a respiratory mask 1 according to the invention, which mask is particularly suitable for introducing the air exhaled by an individual into a measurement device for carrying out an analysis method according to the invention. The respiratory mask 1 is a respiratory mask to be placed centrally over the face.

The respiratory mask 1 has a housing 2 serving as the main body of the respiratory mask, and an air cushion 3 serving as a gas cushion which, on the side of the respiratory mask 1 directed downward in FIG. 4, extends all round the housing 2. During the use of the respiratory mask 1, this side is directed toward the face of the individual wearing the respiratory mask 1.

The housing 2 of the respiratory mask 1 is made of a firm plastic. The basic shape of the housing can be configured in different ways to ensure that individuals with different shapes of faces can apply a respiratory mask 1 that provides the best possible fit.

Two inhalation valves 4 are arranged at the sides of the upper end of the respiratory mask 1, which represents the nose area N of the respiratory mask 1, only one of these inhalation valves being seen in FIG. 4. Air flows through through-openings 40 formed in these inhalation valves 4 and into the space between the respiratory mask 1 and the face of the individual wearing the respiratory mask 1, when the individual breathes in.

An exhalation valve 5 is arranged on the front of the respiratory mask 1, which is arranged at the top in FIG. 4. Air exhaled by the individual flows through through-openings 50 arranged in the exhalation valve 5 when the individual is wearing the respiratory mask 1 correctly and breathes out. Arranged at the center of this exhalation valve 5, there is a minimally conical attachment 6, which has an internal diameter of 22 mm. Air exhaled by the individual is carried off through this attachment 6. For this purpose, it is possible to use a tube (not shown here) connected to the attachment 6.

By virtue of the specific arrangement of the inhalation valves 4, on the one hand, and of the exhalation valve 5, on the other hand, and of the configuration of the inhalation valves 4 and of the exhalation valve 5, it is possible to ensure separation of the inhaled air from the exhaled air of the individual wearing the respiratory mask 1. In addition, the mixing volumes and dead volumes in the respiratory mask are minimized by the arrangement of the inhalation valves 4 and of the exhalation valve 5.

The housing 2 further comprises a conical gas attachment 7 through which oxygen or a gas mixture can, if necessary, be introduced into the space between the respiratory mask 1 and the face of the individual wearing the respiratory mask 1. In this way, it is possible, for example, to provide an additional supply of oxygen to the individual wearing the respiratory mask 1.

A rubber band (not shown in FIG. 4) is secured on holders 8 serving as securing elements, which can be in the form of eyelets or nipples, for example, this band ensuring a secure hold of the respiratory mask 1 on the face of the individual wearing the mask. Instead of a rubber band, other holding means could also be used. The holders 8 are arranged in each case in pairs in the nose area N at the top end and in the mouth area M at the bottom end of the respiratory mask 1.

The air cushion 3 of the respiratory mask 1 has a valve 9 arranged in the mouth area M of the respiratory mask 1 with a Luer connector through which the quantity of air in the air cushion 3 can be regulated. This possibility of adaptation allows the respiratory mask 1 to be optimally adapted to the shape of the face of the individual wearing the respiratory mask 1.

A pressure sensor 10 is also integrated into the air cushion 3 in order to allow the pressure in the air cushion 3 to be measured. For this purpose, a cable connection 11 arranged on the front of the mask housing extends from the pressure sensor 10 to the exhalation valve 5. In the area of the exhalation valve 5 and of the attachment 6 mounted on the exhalation valve, the cable connection 11 has a plug connection 12 onto which a further cable connection for controlling or reading the pressure sensor can be attached.

By means of the pressure sensor 10, it is possible to detect whether the respiratory mask 1 is sitting on the face of an individual or not. The contact pressure afforded by the rubber bands leads to a pressure increase in the air cushion 3. Based on this change in pressure and on the pressure profile over the course of time, it is possible to determine the times at which the respiratory mask 1 is firmly fitted in place. Moreover, an (undesired) removal of the respiratory mask by the individual can be automatically registered. This control possibility via the pressure sensor 10 integrated into the air cushion 3 is also conceivable in many situations and in other respiratory masks with air cushions (e.g. in intensive care medicine).

Figure 5:
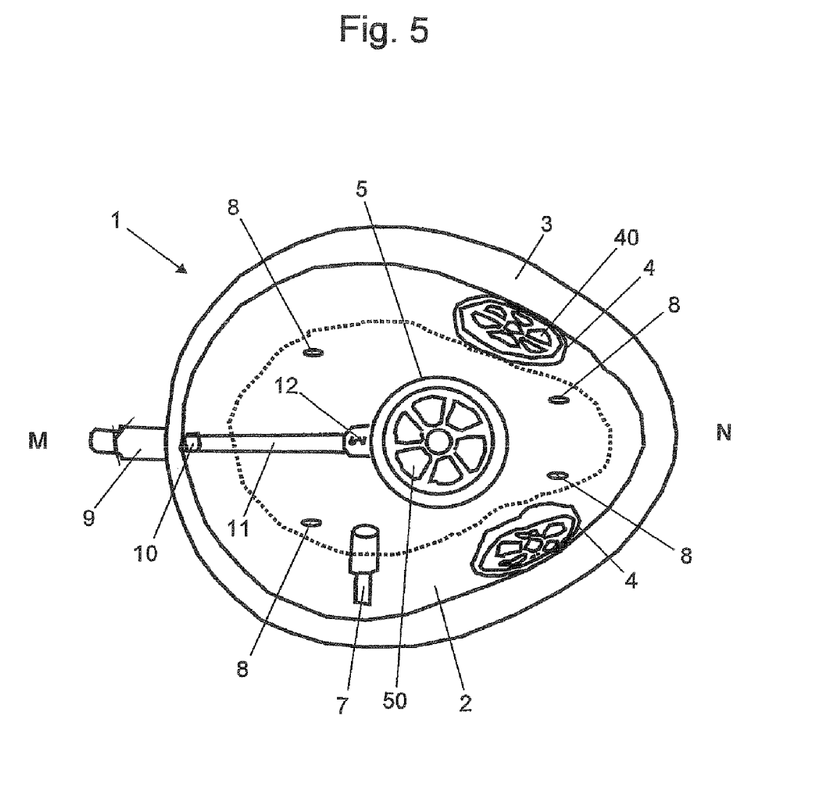
FIG. 5 is a plan view of the respiratory mask from FIG. 4.

FIG. 5 shows a top view of the front of the respiratory mask 1 from FIG. 4. For an explanation of the respiratory mask 1, reference is made to the same reference numbers for the elements already discussed in FIG. 4. In a view complementing that of FIG. 4, FIG. 5 clearly illustrates the lateral arrangement of the exhalation valves 4 and the paired arrangement of the holders 8 in the nose area N and in the mouth area M of the respiratory mask 1.

What is claimed is:

1. An analysis method for determining a functional parameter of a liver of a human or animal individual by measuring the $^{13}CO_2$ content in the air exhaled by the individual to whom or to which a substrate has been administered, the reaction of which in the body of the individual results in the air exhaled by the individual containing $^{13}CO_2$, the method being carried out using a measurement device,
wherein the substrate is $^{13}C$-labeled methacetin, administered intravenously as a bolus in an amount of at least 2 mg per kg bodyweight of the individual,
wherein the measurement device continuously analyzes the $^{13}CO_2$ content in the air exhaled by the individual, the analysis being carried out as a continuous online measurement and analysis,
wherein the functional parameter of the liver is selected from the group consisting of the liver function capacity and the microcirculation in the liver,
wherein the liver function capacity is quantifiably determined from the maximum reaction rate of the substrate in the body of the individual,
wherein the microcirculation in the liver is quantifiably determined from the inundation time, wherein the inundation time is the time needed to reach the maximum reaction rate of the substrate in the body of the individual after administration of the substrate,
wherein the maximum reaction rate is determined by means of zero-order enzyme kinetics via a change over the measurement time of the measured $^{13}CO_2$ content of the air exhaled by the individual,
wherein
if liver function capacity is quantifiably determined, then the maximum reaction rate is standardized by a division by the bodyweight of the individual; and
if the microcirculation in the liver is quantifiably determined, then at least one of the inundation time and the maximum reaction rate is standardized by a division by the bodyweight of the individual,
wherein the $^{13}CO_2$ content is determined relative to the $^{12}CO_2$ content in the air exhaled by the individual, and
wherein the maximum reaction rate of the substrate in the body of the individual is determined by means of the following formula:

$$LiMAx = \frac{(\delta^{13}C_{tmax} - \delta^{13}C_{t0}) \cdot R_{PDB} \cdot P \cdot M}{KG},$$

where $\delta^{13}C$ is the difference between the $^{13}CO_2/^{12}CO_2$ ratio in the air exhaled by the individual and that of the Pee Dee Belmnite standard in delta per mil, $R_{PDB}$ is the $^{13}CO_2/^{12}CO_2$ ratio of the Pee Dee Belmnite standard, P is the $CO_2$ production rate of the individual, M is the molecular weight of the substrate, and KG is the bodyweight of the individual.

2. The analysis method as claimed in claim 1, wherein the $^{13}CO_2$ content of the total air exhaled by the individual is determined from the absolute $^{13}CO_2$ concentration per unit of volume.

3. The analysis method as claimed in claim 2, wherein the maximum reaction rate of the substrate in the body of the individual is determined by means of the following formula:

$$LiMAx = \frac{\int_{t=t_{max}}^{t=t_{max}+i} [^{13}CO_2]dt \cdot \int_{t=t_{max}}^{t=t_{max}+i} \dot{V}dt \cdot M}{KG}$$

where $[^{13}CO_2]$ is the absolute $^{13}CO_2$ concentration per unit of volume, $\dot{V}$ is the volume per unit of time, t is the time, tmax is the time of maximum metabolism, i is the smallest possible time resolution according to the measuring methodology, M is the molecular weight of the substrate, and KG is the bodyweight of the individual.

4. The analysis method as claimed in claim 1, wherein a $CO_2$ production rate of the individual is determined from the body surface area of the individual.

5. The analysis method as claimed in claim 1, wherein the $^{13}C$-labeled methacetin as substrate is administered intravenously as a solution having a pH value of 7.5 to 9.5.

6. The analysis method as claimed in claim 1, wherein the $^{13}C$-labeled methacetin as substrate is administered intravenously as a solution having a methacetin concentration of 0.2 to 0.6% (w/v).

7. The analysis method as claimed in claim 1, wherein the liver function capacity of the individual is classified within a comparison population.

8. The analysis method as claimed in claim 1, wherein microcirculation disturbances in the liver of the individual are assessed by determining the inundation time.

9. The analysis method as claimed in claim 1, wherein the individual is evaluated before a partial liver resection.

10. The analysis method as claimed in claim 1, wherein the individual is evaluated after a partial liver resection.

11. The analysis method as clamed in claim 10, wherein the individual is evaluated after about 1, 2, 3, 5 or 10 days after the partial liver resection.

12. The analysis method as claimed in claim 1 to evaluate liver disorders in an individual.

\* \* \* \* \*